(12) United States Patent
Fishman

(10) Patent No.: US 11,045,667 B2
(45) Date of Patent: Jun. 29, 2021

(54) REAL-TIME X-RAY DOSIMETRY IN INTRAOPERATIVE RADIATION THERAPY

(71) Applicant: Sensus Healthcare, Inc., Boca Raton, FL (US)

(72) Inventor: Kalman Fishman, Boca Raton, FL (US)

(73) Assignee: SENSUS HEALTHCARE, INC., Boca Raton, FL (US)

( * ) Notice: Subject to any disclaimer, the term of this patent is extended or adjusted under 35 U.S.C. 154(b) by 393 days.

(21) Appl. No.: 16/038,807

(22) Filed: Jul. 18, 2018

(65) Prior Publication Data

US 2019/0022418 A1     Jan. 24, 2019

Related U.S. Application Data

(60) Provisional application No. 62/534,010, filed on Jul. 18, 2017.

(51) Int. Cl.
  *A61N 5/10*        (2006.01)
  *G01T 1/161*       (2006.01)
  (Continued)

(52) U.S. Cl.
  CPC ......... *A61N 5/1071* (2013.01); *A61N 5/1014* (2013.01); *A61N 5/1075* (2013.01);
  (Continued)

(58) Field of Classification Search
  CPC .. A61N 5/1071; A61N 5/1014; A61N 5/1075; A61N 5/1083; A61N 2005/1022;
  (Continued)

(56) References Cited

U.S. PATENT DOCUMENTS

| 4,401,406 A | 8/1983 | Rovira |
| 5,621,214 A | 4/1997 | Sofield |

(Continued)

FOREIGN PATENT DOCUMENTS

| CN | 204951972 U | 1/2016 |
| DE | 102010009276 A1 | 8/2011 |

(Continued)

OTHER PUBLICATIONS

International Search Report mailed in PCT/IB2018/055352 dated Nov. 26, 2018.

(Continued)

*Primary Examiner* — Kaylee R Wilson
(74) *Attorney, Agent, or Firm* — Fox Rothschild LLP

(57) ABSTRACT

Real-time X-ray dosimetry sensing in intraoperative radiation therapy (IORT). According to one aspect, a treatment head comprises at least one X-ray component configured to facilitate generation of therapeutic radiation in the X-ray wavelength range. A resilient balloon is disposed over the treatment head and configured for receiving therein a fluid to facilitate X-ray treatment of a tumor cavity. A plurality of X-ray sensing elements is disposed at a plurality of locations distributed on the interior or exterior of the resilient balloon and configured for sensing X-ray radiation emanating from the treatment head. A control system is provided that is responsive to data received from the X-ray sensing elements to determine a magnitude of X-ray radiation detected at each of the X-ray sensing elements.

15 Claims, 10 Drawing Sheets

(51) Int. Cl.
*G01T 1/02* (2006.01)
*G01T 1/06* (2006.01)
*G01T 1/10* (2006.01)

(52) U.S. Cl.
CPC ............ *A61N 5/1083* (2013.01); *G01T 1/026* (2013.01); *G01T 1/06* (2013.01); *G01T 1/10* (2013.01); *G01T 1/161* (2013.01); *A61N 2005/1022* (2013.01); *A61N 2005/1072* (2013.01)

(58) Field of Classification Search
CPC .... A61N 2005/1072; A61N 2005/1074; G01T 1/161; G01T 1/026; G01T 1/06; G01T 1/10
See application file for complete search history.

(56) References Cited

U.S. PATENT DOCUMENTS

| | | | |
|---|---|---|---|
| 5,635,709 A | 6/1997 | Sliski et al. | |
| 5,635,721 A | 6/1997 | Bardi et al. | |
| 6,144,875 A | 11/2000 | Schweikard et al. | |
| 6,207,952 B1 | 3/2001 | Kan et al. | |
| 6,826,254 B2 | 11/2004 | Mihara et al. | |
| 6,977,987 B2 | 12/2005 | Yamashita et al. | |
| 7,005,623 B2 | 2/2006 | Neuberger et al. | |
| 7,140,771 B2 | 11/2006 | Leek | |
| 7,188,999 B2 | 3/2007 | Mihara et al. | |
| 7,193,220 B1 | 3/2007 | Navarro | |
| 7,200,203 B2 | 4/2007 | Cocks et al. | |
| 7,239,684 B2 | 7/2007 | Hara et al. | |
| 7,263,170 B2 | 8/2007 | Pellegrino | |
| 7,266,176 B2 | 9/2007 | Allison et al. | |
| 7,283,610 B2 | 10/2007 | Low et al. | |
| 7,356,120 B2 | 4/2008 | Main et al. | |
| 7,420,160 B2 | 9/2008 | Delaperriere et al. | |
| 7,505,559 B2 | 3/2009 | Kuduvalli | |
| 7,590,219 B2 | 9/2009 | Maurer, Jr. et al. | |
| 7,605,365 B2 | 10/2009 | Chen et al. | |
| 7,619,374 B2 | 11/2009 | Aoi et al. | |
| 7,656,998 B2 | 2/2010 | Main et al. | |
| 7,686,755 B2 | 3/2010 | Smith et al. | |
| 7,693,257 B2 | 4/2010 | Allison | |
| 7,713,205 B2 | 5/2010 | Fu et al. | |
| 7,894,649 B2 | 2/2011 | Fu et al. | |
| 7,902,515 B2 | 3/2011 | Navarro | |
| 8,050,384 B2 | 11/2011 | Carol et al. | |
| 8,126,114 B2 | 2/2012 | Naylor et al. | |
| 8,139,714 B1 | 3/2012 | Sahadevan | |
| 8,180,020 B2 | 5/2012 | Kilby et al. | |
| 8,183,522 B2 | 5/2012 | Celi de la Torre et al. | |
| 8,295,435 B2 | 10/2012 | Wang et al. | |
| 8,303,476 B2 | 11/2012 | Francescatti et al. | |
| 8,321,179 B2 | 11/2012 | Simon et al. | |
| 8,332,072 B1 | 12/2012 | Schaible et al. | |
| 8,520,801 B2 | 8/2013 | Henning | |
| 8,559,596 B2 | 10/2013 | Thomson et al. | |
| 8,559,598 B2 | 10/2013 | Kindlein et al. | |
| 8,602,647 B2 | 12/2013 | Navarro | |
| 8,655,429 B2 | 2/2014 | Kuduvalli et al. | |
| 8,660,235 B2 | 2/2014 | Koehler | |
| 8,792,613 B2 | 7/2014 | Gardner et al. | |
| 8,804,901 B2 | 8/2014 | Maurer, Jr. et al. | |
| 8,917,813 B2 | 12/2014 | Maurer, Jr. | |
| 8,929,511 B2 | 1/2015 | van der Veen et al. | |
| 8,934,605 B2 | 1/2015 | Maurer, Jr. et al. | |
| 8,989,846 B2 | 3/2015 | Kuduvalli et al. | |
| 8,995,616 B2 | 3/2015 | van der Veen et al. | |
| 9,036,787 B2 | 5/2015 | de Jager | |
| 9,040,945 B1 | 5/2015 | Hayman | |
| 9,076,201 B1 | 7/2015 | Negandar et al. | |
| 9,108,048 B2 | 8/2015 | Maurer, Jr. et al. | |
| 9,168,391 B2 | 10/2015 | Henning et al. | |
| 9,289,268 B2 | 3/2016 | Ramraj et al. | |
| 9,333,031 B2 | 5/2016 | Salahieh et al. | |
| 9,415,239 B2 | 8/2016 | Lubock et al. | |
| 9,561,009 B2 | 2/2017 | Woudstra et al. | |
| 9,616,251 B2 | 4/2017 | Filiberti et al. | |
| 9,724,066 B2 | 8/2017 | Van Der Veen et al. | |
| 9,743,912 B2 | 8/2017 | Fichtinger et al. | |
| 10,327,716 B2 | 6/2019 | Mazin | |
| 10,350,437 B2 | 7/2019 | Fishman | |
| 10,398,519 B2 | 9/2019 | Kim et al. | |
| 10,607,802 B2 | 3/2020 | Fishman et al. | |
| 10,646,726 B2 | 5/2020 | Fishman | |
| 2001/0049475 A1 | 12/2001 | Bucholz et al. | |
| 2002/0077545 A1 | 6/2002 | Takahashi et al. | |
| 2002/0085668 A1 | 7/2002 | Blumhofer et al. | |
| 2002/0136439 A1 | 9/2002 | Ruchala et al. | |
| 2004/0218721 A1 | 11/2004 | Chornenky et al. | |
| 2004/0227056 A1 | 11/2004 | Neuberger et al. | |
| 2005/0101824 A1* | 5/2005 | Stubbs ................ A61N 5/1071 600/3 |
| 2005/0111621 A1 | 5/2005 | Riker et al. | |
| 2005/0276377 A1 | 12/2005 | Carol | |
| 2006/0020195 A1 | 1/2006 | Falco et al. | |
| 2006/0085053 A1 | 4/2006 | Anderson et al. | |
| 2007/0076851 A1 | 4/2007 | Pellegrino | |
| 2008/0009659 A1 | 1/2008 | Smith et al. | |
| 2008/0170663 A1 | 7/2008 | Urano et al. | |
| 2008/0198970 A1 | 8/2008 | Kirshner et al. | |
| 2009/0161826 A1 | 6/2009 | Gertner et al. | |
| 2010/0030463 A1 | 2/2010 | Tomizawa | |
| 2010/0040198 A1 | 2/2010 | Comer et al. | |
| 2010/0237259 A1 | 9/2010 | Wang | |
| 2010/0274151 A1 | 10/2010 | Chi et al. | |
| 2011/0105822 A1 | 5/2011 | Roeder | |
| 2012/0016175 A1 | 1/2012 | Roberts et al. | |
| 2012/0037807 A1* | 2/2012 | Ujhazy ..................... G01T 7/00 250/362 |
| 2013/0025055 A1 | 1/2013 | Saracen et al. | |
| 2013/0116555 A1 | 5/2013 | Kuzelka | |
| 2013/0131428 A1 | 5/2013 | Jiang et al. | |
| 2013/0217947 A1 | 8/2013 | Fishman | |
| 2013/0231516 A1 | 9/2013 | Loo et al. | |
| 2013/0345718 A1 | 12/2013 | Crawford et al. | |
| 2014/0054465 A1 | 2/2014 | Berke | |
| 2014/0086388 A1 | 3/2014 | Yamada et al. | |
| 2014/0105361 A1 | 4/2014 | Vogtmeier et al. | |
| 2014/0121501 A1 | 5/2014 | Fichtinger et al. | |
| 2014/0171919 A1 | 6/2014 | Blacker | |
| 2014/0185778 A1 | 7/2014 | Lee et al. | |
| 2014/0205067 A1 | 7/2014 | Carol et al. | |
| 2014/0348288 A1 | 11/2014 | Boyd et al. | |
| 2015/0265306 A1 | 9/2015 | Andrews | |
| 2015/0265353 A1 | 9/2015 | Andrews | |
| 2015/0265366 A1 | 9/2015 | Andrews | |
| 2015/0366546 A1 | 12/2015 | Kamen et al. | |
| 2016/0106387 A1 | 4/2016 | Kahn et al. | |
| 2016/0184032 A1 | 6/2016 | Romo et al. | |
| 2016/0193482 A1 | 7/2016 | Fahrig et al. | |
| 2017/0001939 A1 | 1/2017 | Sookraj et al. | |
| 2017/0004267 A1 | 1/2017 | Svatos et al. | |
| 2017/0296289 A1 | 10/2017 | Andrews et al. | |
| 2017/0368369 A1 | 12/2017 | Heinrich et al. | |
| 2018/0015303 A1 | 1/2018 | Fishman | |
| 2018/0286623 A1 | 10/2018 | Fishman et al. | |
| 2019/0022418 A1 | 1/2019 | Fishman | |
| 2019/0060674 A1 | 2/2019 | Fishman | |
| 2020/0038691 A1 | 2/2020 | Fishman et al. | |
| 2020/0101325 A1 | 4/2020 | Ollila et al. | |
| 2020/0121957 A1 | 4/2020 | Fishman et al. | |

FOREIGN PATENT DOCUMENTS

| | | |
|---|---|---|
| RU | 2013147424 A | 4/2015 |
| WO | 2010030463 | 3/2010 |
| WO | 2010065740 A2 | 6/2010 |
| WO | 2017044441 A | 3/2017 |

OTHER PUBLICATIONS

(56) References Cited

OTHER PUBLICATIONS

Extended European Search Report dated Jan. 31, 2020 in EP 17828486.5 filed Jan. 23, 2019.
International Search Report dated Aug. 8, 2018 in PCT/US18/25438.
International Search Report dated Sep. 21, 2017 in PCT/US17/041986.
International Search Report and Written dated Oct. 29, 2018 in PCT/US18/46663.
International Search Report and Written Opinion dated Feb. 19, 2020 in PCT/US19/57191.
Extended European Search Report dated Jul. 9, 2020 in EP 18776334.

* cited by examiner

REAL-TIME X-RAY DOSIMETRY IN INTRAOPERATIVE RADIATION THERAPY

CROSS REFERENCE TO RELATED APPLICATIONS

This application claims the benefit of U.S. Patent Provisional No. 62/534,010, filed on Jul. 18, 2017, which is hereby incorporated by reference in its entirety.

BACKGROUND

Statement Of The Technical Field

The inventive arrangements relate to radiation therapy, and more particularly to systems and methods for intraoperative radiation therapy.

DESCRIPTION OF THE RELATED ART

Cancer surgery can involve removal of a cancerous tumor and some normal tissue surrounding the tumor. For example, Breast Conserving Surgery (BCS) is a type of cancer surgery in which a cancerous lump and part of the surrounding breast tissue (as opposed to the entire breast) is removed during surgery. The surgery is usually followed by a moderate-dose radiation therapy which is intended to eradicate any traces of cancerous tissue from a tumor bed (vascular and stromal tissue that surrounds a cancerous tumor). Radiotherapy techniques can involve an externally delivered radiation dose using a technique known as external beam radiotherapy (EBRT). But conventional EBRT can increase the risk of missing an intended target volume. To address this problem, intraoperative radiotherapy (IORT) is sometimes used. IORT involves the application of therapeutic levels of radiation to a tumor bed while the area is exposed and accessible during excision surgery. The benefit of IORT is that it allows a high dose of radiation to be delivered precisely to the targeted area with minimal exposure to surrounding tissues. IORT also avoids the usual delays which are associated with the time between when the surgical removal of the cancerous tissue and the EBRT.

When IORT is appropriate a surgeon will remove a cancerous tumor after which a radiation oncologist will position a radiation applicator or treatment within the patient, in the area where the tumor was previously located. Such a treatment head can generate low energy X-Rays within the tumor cavity from which the cancerous tumor was removed.

SUMMARY OF THE INVENTION

This document concerns a method and system for real-time X-ray dosimetry. The method involves disposing an X-ray treatment head within an inflatable balloon. The balloon is inflated, after which X-ray energy is applied using the X-ray treatment head, to a treatment surface which is external of the balloon. The method further involves detecting an X-ray dose delivered by the treatment head to at least one portion of the treatment surface. This result is achieved by using at least one sensing element which is attached to a wall which forms the balloon.

According to one aspect, the detecting step described herein can involve detecting the X-ray dose delivered from the treatment head to a plurality of locations associated with different portions of the treatment surface. This is accomplished by using a plurality of the sensing elements attached to a plurality of different locations on the balloon. In some scenarios, the plurality of different locations can be aligned with locations where a plurality of orthogonal axes (e.g., centered on the X-ray treatment head), will intersect the surface of the balloon, when the balloon is inflated. In other scenarios the plurality of different locations may define an ovoid or spherical grid pattern on the surface of the balloon (when the balloon is inflated).

In a solution presented herein, sensed data from the one or more sensing elements is communicated from the at least one sensing element to an electronic control system. According to one aspect, the communication of the sensed data from the at least one sensing element to the electronic control system is facilitated by using conductive wire lead, an optical fiber, and/or a wireless data transceiver.

In some scenarios, the one or more sensing elements provided on the balloon may be comprised of a semiconductor material, a silicon drift detector (SDD), and/or a PIN diode type of X-ray detector. In other scenarios, the sensing element can be selected so as to fluoresce or change color when exposed to the X-ray energy. In those instances where a sensing element is configured to fluoresce or change color, an X-ray dose indicated or detected by the at least one sensing element can be determined based on an intensity of fluorescence or color change exhibited by the at least one sensing element. For example, an X-ray dose detected by the at least one sensing element can be determined by using an image capture device that is disposed within the balloon. The image capture device in such scenarios can detect at least one of a fluorescence or color change of the at least one sensing element.

The solution also concerns a system for real-time X-ray dosimetry. The system includes an inflatable balloon which is configured to receive within an interior thereof an X-ray treatment head from which X-rays can be emitted. At least one sensing element is attached to a wall which forms a surface of the balloon. The sensing element is responsive to X-ray energy and configured to communicate information concerning an X-ray dose detected by the sensing element. More particularly, the sensing element can communicate X-ray dose information detected at a sensing location where the at least one sensing element is attached to the wall.

According to one aspect, a plurality of the sensing elements are attached to a plurality of different sensing locations on the balloon. For example, the plurality of different sensing locations can be aligned with locations where a plurality of orthogonal axes having an origin at an approximate center of the balloon, intersect the surface of the balloon, when the balloon is inflated. In other scenarios, the plurality of different sensing locations define an ovoid or spherical grid pattern on the surface of the balloon under a conditions in which the balloon is inflated.

The at least one sensing element included in the system is advantageously selected from the group consisting of a sensor formed of a semiconductor material, a silicon drift detector (SDD), and a PIN diode detector. The system will further include at least one information communication component which is configured to facilitate communication of sensor information from the at least one sensing element to an electronic control system. In some scenarios, the information communication component can be a conductive wire lead, an optical fiber, and/or a wireless data transceiver.

In other scenarios, the at least one sensing element is configured to fluoresce or change color when exposed to the X-ray energy. In such instances, an image capture device can be disposed within the balloon. Further, the image capture device is configured to facilitate acquisition of image information indicating at least one of a fluorescence or color change of the at least one sensing element. The image capture device is communicatively coupled to an electronic control system. The electronic control system is configured to evaluate the fluorescence or color change as a basis for determining an X-ray dose received at the at least one sensing element.

The solution disclosed herein also includes an X-ray dosimetry sensing system where the inflatable balloon includes a multiplicity of sensing elements disposed at distributed locations on a wall which forms a surface of the balloon, where each of the plurality of sensing elements is responsive to X-ray energy. The sensing elements in such a solution are each configured to communicate information concerning an X-ray dose detected by the sensing element at a sensing location where the sensing element is attached to the wall.

BRIEF DESCRIPTION OF THE DRAWINGS

The disclosure herein will be with reference to the following drawing figures, in which like numerals represent like items throughout the figures, and in which.

DETAILED DESCRIPTION

Figure 1:
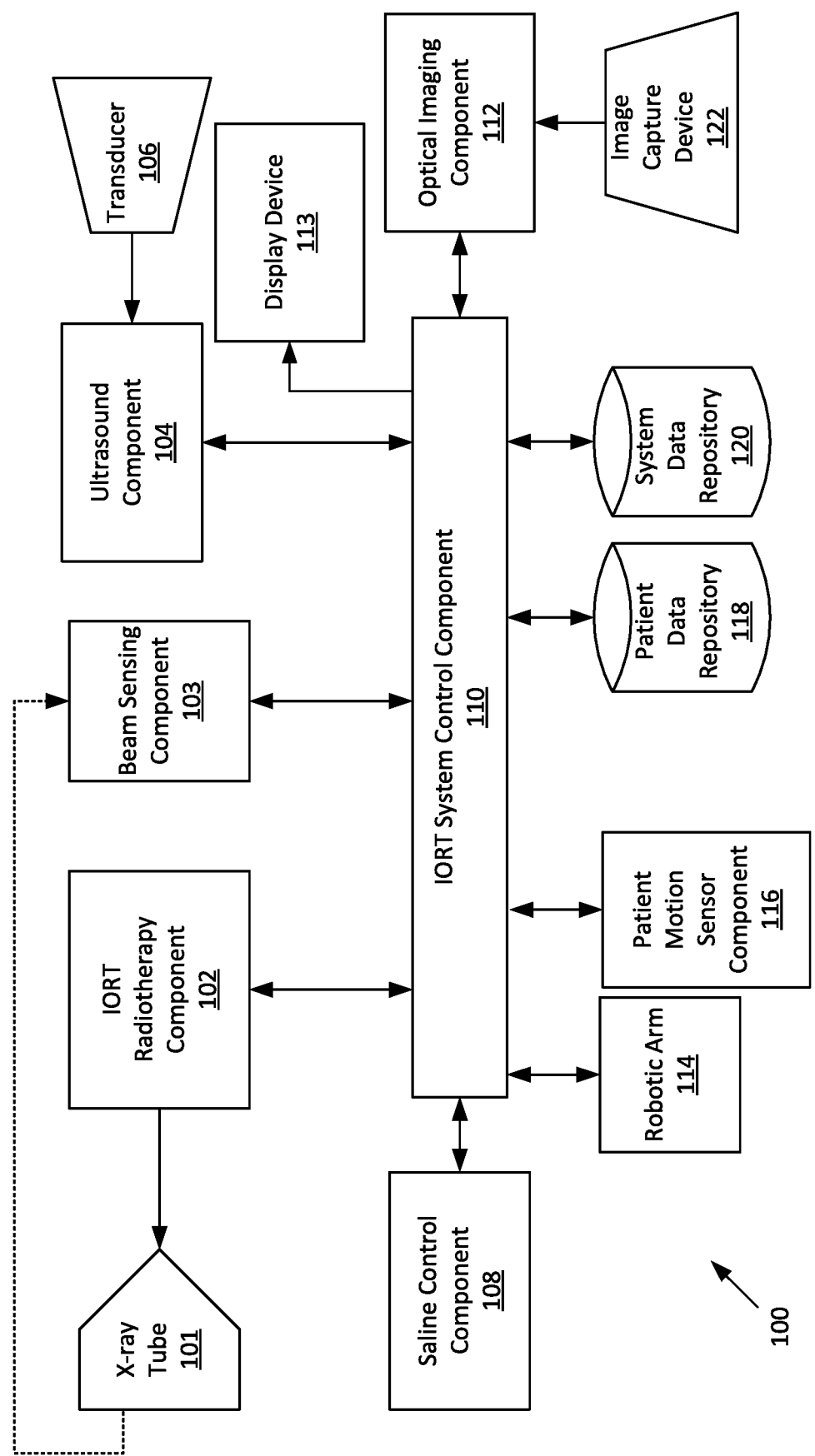
FIG. 1 is a block diagram that is useful for understanding a robotic IORT system.

It will be readily understood that the components of the systems and methods described herein and illustrated in the appended figures could be arranged and designed in a wide variety of different configurations. Thus, the following more detailed description, as represented in the figures, is not intended to limit the scope of the present disclosure, but is merely representative of certain exemplary scenarios which are useful for understanding the disclosure. While the various aspects are presented in drawings, the drawings are not necessarily drawn to scale unless specifically indicated.

One type of low energy X-Ray IORT applicator involves a catheter-like device with a balloon tip. After a tumor has been excised, the catheter is inserted into the cavity where the tumor was previously located, a miniature radiation therapy source is then inserted within the balloon into the cavity to deliver radiation to the tumor bed internally and the balloon is inflated with saline such that the inflated balloon fits snugly within the cavity. The balloon and saline solution are used to help ensure that a homogeneous radiation dose is applied to all portions of the tumor bed. The saline is used to inflate the balloon and reduces radiation attenuation as normally occurs when x-rays travel through air. The saline solution is also constantly circulated within the balloon in order to provide a redundant coolant medium for the X-Ray miniature source during therapy. After a period of time (e.g., 15 minutes) the radiation source and balloon are removed from the cavity and the surgeon closes the incision.

The expense and short operating life associated with miniature X-ray sources can easily be overcome by larger more conventional X-ray sources. But these sources present a different problem when performing IORT. It is important when performing IORT to maintain all of the tissue of the tumor bed at a predefined distance from the radiation source. This ensures homogeneous radiation exposure to the entire tumor bed. A larger more conventional X-ray source must normally be supported on an articulating arm. The articulating arm holds the X-ray source in a fixed position. In contrast, the respiratory function of a patient means that the tissue in and around the chest cavity will be in constant motion. So relative motion between the source and the cavity walls forming the tumor bed make it nearly impossible to ensure that a homogeneous radiation dose is applied to all of the tissue comprising the tumor bed.

A solution to this problem is robotic IORT in which the X-ray source is disposed on a robotic arm. The movement of the robotic arm is synchronized with the respiratory action of the patient so that the X-ray source always has the same relative position to the tissue comprising the tumor bed. The robotic arm supports the X-ray source and provides all necessary utility channels to support IORT functions and operations. For example, the robotic arm can provide primary electric power for operating the X-ray source. The robotic arm can also include one or more liquid conduits to facilitate delivery of saline to an inflatable balloon and for draining saline from the balloon.

With the foregoing arrangement, a more conventional or larger size X-ray source can be used for IORT in place of a miniaturized X-ray source. The conventional X-ray source can provide all of the benefit of a miniature X-ray source but without the added cost associated with the miniature X-ray source. The functional result for the patient is the same as with the miniature X-ray source disposed in a flexible catheter, but the durability and lower cost of the larger conventional X-ray source will greatly reduce the overall cost of IORT treatment. The larger type of X-ray source as described here can also include a balloon disposed over the X-ray treatment head which is inserted into the tumor cavity. The balloon can be inflated or deflated by controlling a flow of saline to the interior cavity of the balloon.

As noted above, an inflatable balloon disposed around the X-ray radiation source in the treatment head can help ensure that a homogeneous radiation dose is applied to all portions of the tumor bed. One aspect of the balloon concept is that, when properly inflated, it urges all of the tissues comprising the tumor bed to conform to a roughly spherical shape as defined by the inflated balloon. Consequently, a radiation source disposed in the center of the balloon will be approximately equidistant from all of the tissue surfaces which define the tumor bed. If the radiation source has an approximately spherical or isotropic radiation pattern, then the result will be a substantially homogeneous radiation dose being applied to all portions of the tumor bed.

Still, there are some problems with this approach which can result in unwanted variations in the amount of X-ray radiation that is applied to various portions of the tumor bed. For example, the radiation source, because of its design or due to a malfunction, may not produce an expected X-ray radiation pattern. Alternatively, the balloon may not truly achieve an expected spherical shape within the tumor bed. Either such scenario can lead to different portions of the tumor bed receiving different or inconsistent levels of X-ray radiation.

Further, recent developments with X-ray treatment heads used for IORT have the potential to facilitate X-ray beam steering within the tumor cavity. But there is currently no good method to verify that a beam steering operation has occurred properly and/or is delivering a desired amount of X-ray radiation to a particular portion of a tumor bed.

Accordingly, the present solution involves a system for real-time monitoring of X-ray dosimetry within the context of IORT. The solution involves a plurality of X-ray radiation sensor elements (XRSE) which are disposed on the surface of the balloon or integrated with the balloon. In some scenarios, the sensors are disposed on the interior of the balloon. In other scenarios, the sensors are disposed on the exterior of the balloon. In still other scenarios, the sensors can be integrated with the material forming the balloon.

The XRSE are disposed at a plurality of predetermined locations. In some scenarios, these locations can be aligned with each of a plurality of orthogonal axis which define an x, y and z coordinate system, with the X-ray radiation source aligned at the origin where the axis intersect. In other scenarios, the plurality of XRSE can be aligned with a plurality of points which define a spherical grid. The term spherical grid as used herein can be a set of points which are uniformly (or semi-uniformly) disposed over the surface of an approximately spherical shape as defined by the balloon.

The sensors disclosed herein can be disposed on a surface of the balloon or embedded in the balloon. As such the balloon can comprise a specialized design and can involve a unique fabrication process to facilitate unique and novel tissue management balloons for radiotherapy. The balloons can be fully integrated with embedded x-ray sensors for real time dosimetry feedback and controls.

The XRSE will communicate the result of their sensing activities to a control system, which monitors the X-ray radiation dose detected by each of the sensors. Each XRSE will have a known location on the surface of the balloon, and this location will be known to the control system. Consequently, the control system can determine the exact dose of X-ray applied in radial directions aligned with each of the XRSE. These results can be displayed to a treatment specialist on a computer display. The treatment specialist can thereby monitor in real time the actual amount of X-ray radiation applied by an X-ray source to the tumor bed, and can do so with respect to various radial directions defined relative to the X-ray source. The detected radiation levels from each of the XRSE can also be used by the treatment specialist to help position the X-ray treatment head. For example, in some scenarios, the treatment specialist can adjust the position of a treatment head containing an X-ray source so that greater uniformity in X-ray intensity is achieved within the tumor cavity. As explained below in further detail, these adjustments can be performed manually or by means of a robotic arm.

It will be appreciated that when the balloon which surrounds the X-ray source is inflated to different degrees, the positions of the XRSE for different inflation volumes/pressure of saline will necessarily change. But the actual locations and distance between the X-ray source and each XRSE can be known in advance. By carefully controlling an amount of saline pumped into the balloon, and/or saline pressure within the balloon and measuring the resulting distance from the XRSE to the X-ray source it is possible to determine the XRSE positions distance to the source under various conditions. Alternatively, the characteristics of the balloon can be modeled using computer software so that the radius of the inflated balloon is known for different conditions. This additional information can be useful for purposes of accurately presenting the treatment information to a technician or treatment specialist.

The various aspects of the present disclosure will be described with respect to the attached drawings of an exemplary system that can deliver both therapeutic IORT functionalities through a single platform to better serve and benefit the practitioner and patient. The exemplary system can include multiple imaging devices and a radiotherapy device used cooperatively to perform IORT in accordance with the present disclosure. In some scenarios, the system can involve use of a robotic IORT system.

As explained below in further detail, the robotic IORT system can use a robotic arm to help ensure a consistent position of an X-ray source used during IORT. The robotic arm can facilitate controlled movement of the X-ray source disposed within the patient in response to autonomic motions of the patient associated with breathing and the like. As explained below in further detail, such motion control can be facilitated by use of force sensors disposed in the robotic arm, or by means of fiducial markers disposed on the patient to track such movements. But the present disclosure creates the opportunity for a further means of evaluating the effect of such motion on the actual applied radiation dose at locations within the tumor cavity. Accordingly, variations in detected X-ray radiation levels caused by such breathing activity can be actually measured at different locations within the tumor cavity. These variations can be communicated to the control system and can provide a further basis upon which to control the robotic arm. In response to detected variations in X-ray radiation at the various XRSE, the robotic arm can automatically move the X-ray source to provide a more uniform dose. These and other features of the present solution will become apparent from the description below.

Referring now to FIG. 1 there is shown a high level block diagram representation of a robotic IORT system 100 which is useful for understanding the invention. The exemplary system 100 can include a radiotherapy component 102 with X-ray tube 101, an optional ultrasound component 104 with a transducer 106, an optical imaging (OI) component 112 with an associated image capture device (ICD) 122. The system also includes a robotic arm 114, patient motion sensor 116, and a saline control component 108. The system control component 110 guides the robotic arm 114 during IORT operations based on images and data obtained from one or more of a patient motion sensor component 116, the ultrasound component 104, transducer 106, OI component 112, and ICD 122.

The saline control component can comprise a pump and one or more selectively controlled valves, all under the control of software and hardware elements associated with the system control component. The pump can be connected to a reservoir or source of saline solution. As such, the saline control component can control a flow of saline to and from a balloon (not shown) disposed on the end of a robotic arm 114. When IORT operations are to be performed, the balloon is inserted into a cavity from which a cancerous tumor has been removed and is inflated with saline. Once inflated, the X-ray tube 101 and radiotherapy component 102 are used to apply radiation to the walls of the cavity formed by the tumor bed. During the application of radiation, the saline control component can monitor and maintain fluid circulation and pressure within the balloon. After IORT treatment has been completed, the saline control component 108 releases the saline to deflate the balloon and the balloon is withdrawn from the cavity.

The robotic arm 114 is advantageously selected to be a robotic system that provides freedom of movement about multiple orthogonal axes (e.g. up to seven axes) and includes lightweight force and torque sensors (not shown) to ensure safe operation with humans without the need for a safety fence. Exemplary robots of this kind are commercially available from various sources. For example, KUKA Roboter GmbH of Augsburg Germany (KUKA) manufactures a line of direct human-robot collaboration (HRC) capable lightweight robots which are suitable for direct human-robot interaction. These robots include the LBR iiwa model produced by KUKA. Robots of this kind are well suited for the delicate operations described herein because they include joint torque sensors which can detect contact with objects, and can respond by immediately reducing a level of force and speed associated with robot movements.

The patient motion sensing component 116 can include optical sensors, ultrasound sensors, pressure sensors, laser sensors or any other type of sensor which is useful for monitoring movement of a patient undergoing IORT treatment. For example, such movement may comprise respiratory movement and/or digestive system movement which occurs during IORT. The patient motion sensor component can be separate from the robotic arm 114 and/or may be integrated into the robotic arm to facilitate such sensing. In some scenarios, data from ultrasound component 104, transducer 106, optical imaging component 112, and image capture device 122 can be used for patient motion sensing as described herein. The information from these sensors can be used instead of or in conjunction with sensing data acquired from patient motion sensor component 116.

The system control component 110 receives the patient motion sensor data and uses it to control the robotic arm 114. More particularly, during IORT operations as described herein, a motion of the robotic arm is controlled in accordance with the patient motion sensing data to ensure that the X-ray tube 101 moves in sync with the tissue natural movement due to respiratory or other body functions, which will precisely align the X-Ray source relative to the tumor bed which is receiving radiation therapy. The precise control over the motion and position of the X-ray tube can ensure that all areas of the tumor bed receive a homogenous exposure to the applied radiation. In order to accomplish this result, the robotic arm can move along multiple motion axes (e.g., up to seven motion axes) to maintain its relative position within the cavity from which the cancerous tumor was removed.

The radiotherapy component 102 is utilized to treat a tumor bed in accordance with IORT treatment methods which are now known or known in the future. The X-ray tube 101 is advantageously selected to be an isotropic source for x-ray photon particles to perform IORT of a tumor bed. Further, the X-ray tube is advantageously selected and purposely designed so that it has a relatively small size such that it fits within a cavity from which a cancerous tumor has been removed, yet it is robust and large enough to withstand numerous treatment sessions without burning out, or failing. This approach and design will provide a cost-effective solution for a reusable IORT X-Ray source, which is small enough to fit in most or all post-surgical tumor bed cavities, yet not too physically small, which translates to very short life spans and higher costs of utilization.

The radiotherapy component 102, which can be a superficial radiotherapy component, and X-ray tube 101, can together include control circuitry, one or more cooling elements for the X-ray tube, power supplies, one or more high voltage generator, one or more interchangeable applicators, and one or more hardware timers that work in concert with a software timer for redundancy and other purposes. It is contemplated that the X-ray tube utilized herein will be selected so that is optimized for IORT interaction with tumor bed tissue, and has minimal effects at deeper tissue depths. For example, a conventional superficial radiation therapy (SRT) type of X-ray unit can be used for this purpose. As will be appreciated, an SRT type of X-ray unit produces low energy X-rays that is suitable for this purpose.

In some scenarios, a solid-state X-ray beam sensing component 103 can monitor the beam output of the radiotherapy component 102 and x-ray tube 101, along with overall system stability and yield. The solid-state X-ray beam sensing component 103 is mounted to the X-Ray tube 100 and is moved in front of the tube when the system 150 needs to be tested for quality control, or overall system 150 diagnosis purposes. Otherwise, it is retracted back in its home position, away from the X-ray tube 101 and the X-ray beam in order not to interfere during a IORT operations as described herein.

The present disclosure contemplates that in addition to or as an alternative to using a X-ray based radiotherapy in system 100, any other types of radiotherapy can be used in system 100. Thus, the components for radiotherapy can be selected to support photon-based radiotherapy (e.g., x-rays and gamma rays), particle-based radiotherapy (e.g., electrons, protons, neutrons, carbon ions, alpha particles, and beta particles), or any combinations thereof which may be determined to be suitable for IORT now or in the future.

The ultrasound component 104 can include control circuitry, system drivers, operation control software, and a transducer 104, which can be high frequency ultrasonic transducer, for tissue imaging of the tumor bed. The ultrasound component 104 communicates with the software of the system control component 110 via a bus and system drivers. The ultrasound component 104 and transducer 106 are provided in exemplary system 100 to provide structural or anatomical data associated with the tumor bed without exposing a subject to ionizing radiation. However, the present disclosure contemplates that ultrasound component 104 and transducer 106 can be replaced or supplemented in system 100 with components for supporting any other types of imaging techniques that also do not utilize ionizing radiation. For example, optical coherence tomography or laser range scanning (LIDAR), to name a few.

The ultrasound component 104 can be any ultrasound device capable of operating within an acceptable bandwidth. For example, the ultrasound component and transducer 106 can operate in a bandwidth of approximately 2 MHz to approximately 70 MHz, and may be implemented with an electro-mechanical, or a solid state transducer. The system 100 can provide the ultrasound component 104 at least partially integrated inside a system 100 housing coupled to a data bus, with a transducer head 106 outside of the housing as discussed in relation to FIGS. 2 and 3. The ultrasound component 104 and other components of the system 100, can be in communication with a data bus to facilitate communication of image data to system control component 110 and/or display device 113. A suitable interface standard can be used for this purpose such as peripheral component interconnect (PCI/PCIe), universal serial bus (USB/USBII/USBIII/USB-C), Ethernet, or Firewire. However, the present disclosure contemplates that any other interface and/or communications standards can be used.

The optical imaging component 112 can include control circuitry, system drivers, operation control software, and one or more image capture devices 122, for imaging a tumor bed. According to one aspect, the optical imaging component is a spectroscopic imaging device. For example, the optical imaging component can comprise a multispectral imaging device that captures image data at a plurality of optical frequencies. Such multispectral imaging component can be configured to utilize optical energy from the visible portion of the light spectrum for imaging purposes, but can also utilize optical energy from frequencies beyond the visible light range (e.g. infrared and near ultraviolet). Alternatively, the optical imaging component can comprise a hyperspectral imaging device wherein optical information is captured from across the electromagnetic spectrum at each pixel in the captured image. As a further alternative, the spectroscopic imaging device can be configured for Raman spectroscopy which captures changes in the frequency of photons in monochromatic light which result from interaction with tissue within the tumor bed. As a further alternative, the spectroscopic imaging device can be configured for photoacoustic imaging, which utilizes non-ionizing laser pulses or an alternative light source to image the residual cavity tissue.

The optical imaging component 112 communicates with the software of the system control component 110 via a bus and system drivers. The present disclosure contemplates that optical imaging component 112 and the image capture device 122 can be replaced or supplemented in system 100 with components for supporting any other types of imaging techniques for extracting molecular or functional information from tumor bed tissues. For example, biomarkers can be used to enhance the usefulness of the optical imaging methods described herein. As is known, a biomarker can involve a substance which is introduced to a tissue to facilitate the identification of a disease condition such as cancer. According to one aspect, a biomarker can include any substance introduced to a tumor bed tissue which can be used to induce visually or optically detectable changes that can facilitate identification of cancerous cells. Any biomarker now known or known in the future can be used in conjunction with the optical imaging component 112 and the one or more image capture devices 122 provided that it can help facilitate identification of functional data pertaining to tumor bed tissue under observation.

Figure 2:
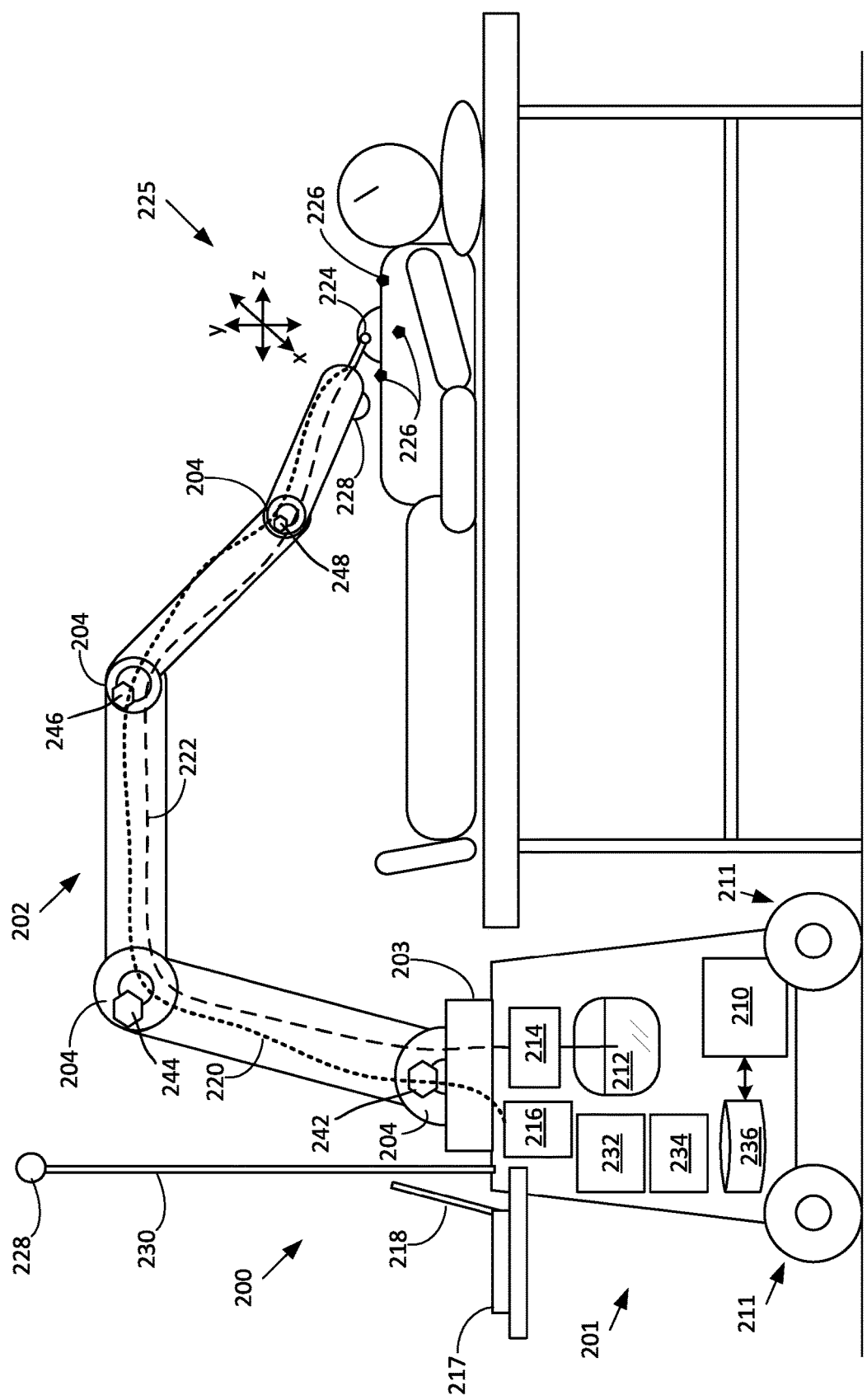
FIG. 2 is a diagram that is useful for understanding an implementation of a robotic IORT using a robotic arm and a treatment head.
Figure 3:
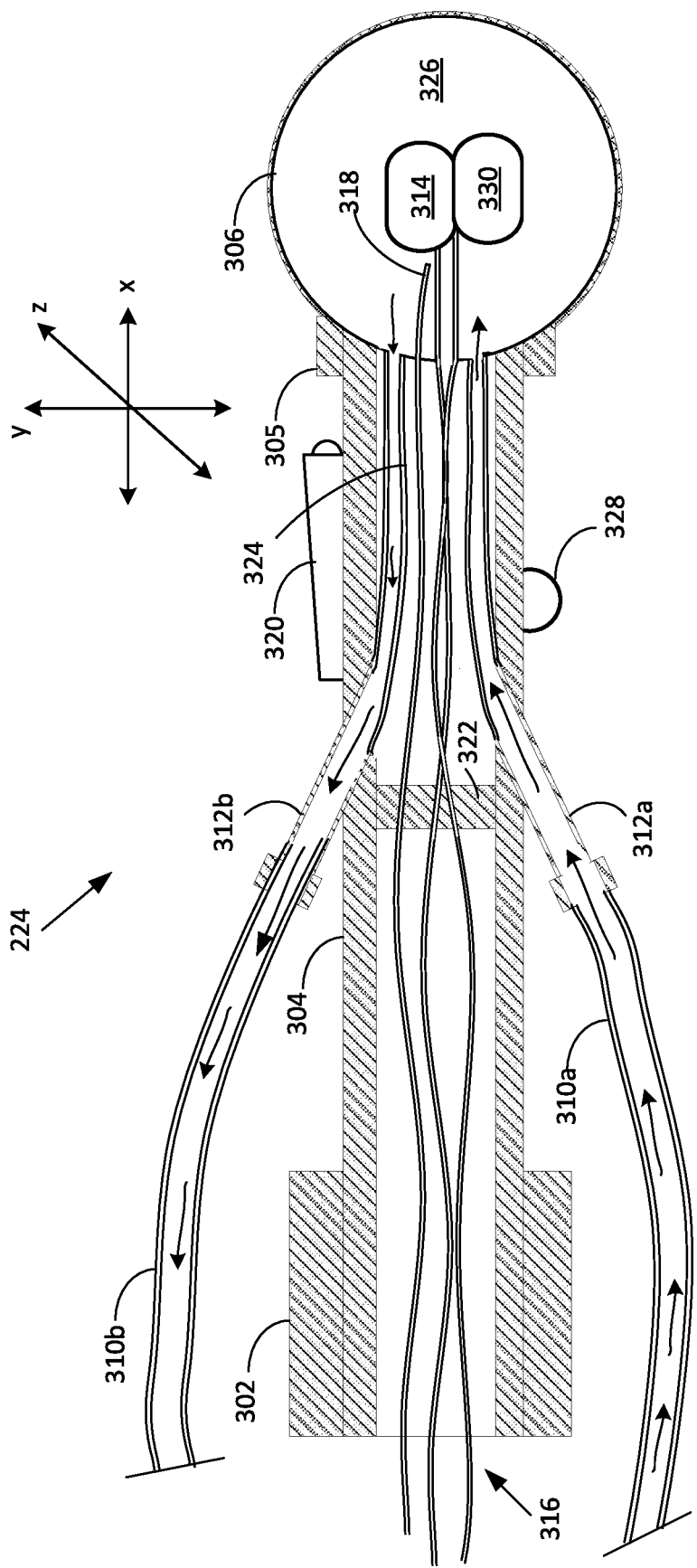
FIG. 3 is a drawing showing a more detailed view of a treatment head disposed on the robotic arm in FIG. 2.

The optical imaging component 112 can be provided at least partially integrated inside a housing of system 100 coupled to data bus with one or more image capture devices 122, outside of the housing as shown in FIGS. 2 and 3. The optical image component 112 and other components of the system 100 can be in communication with the data bus and the respective other components of the system 100 utilizing interface standards such as peripheral component interconnect (PCI/PCIe), universal serial bus (USB/USBII/USBIII/USB-C), Ethernet, or Firewire, to name a few. However, the present disclosure contemplates that any other interface and/or communications standards can be used.

In some scenarios, the system 100 utilizes the ultrasound component 104 with a transducer 106 to scan and image a tumor bed, to obtain structural or anatomical information about the region of interest. The system can also utilize the optical imaging component 112 with image capture device 122 to optically scan and image the same volume to obtain functional and/or metabolic information pertaining to the skin tissue or portions thereof. As used herein, the functional and/or metabolic information referenced herein can include any information pertaining to the biological function, behavior or processes at work in a particular cell or group of cells. The ultrasound and optical scanning processes will be described below in further detail. A registration process can be used to facilitate alignment of the image data acquired using the ultrasound and optical scanning methods. After the region of interest has been scanned and imaged by the system 100, the image data is processed by the system's software. The image data acquired using the ultrasound and optical scanning methods can be registered and then fused or merged to form a single image. In the fused image, the image data acquired by using ultrasound is basically superimposed over the image data acquired by using the optical scanning method described herein. The result is a hybrid image which includes detailed anatomical and/or structural data for the tumor bed with the functional data for the same tissue volume superimposed. This process can be used after tumor excision to help identify any portions of the tumor bed that may comprise cancerous tissue.

The system 100 is controlled and operated by the system control component 110, which can include a central computer with a motherboard that runs operation and control software with various parallel and connected boards that allow it to control, communicate, and monitor the various sub-components and modules of the system 100. This achieves harmonious functionality between the three main clinical components of the system 100 including the radiotherapy component 102, the robotic arm 114 and the patient motion sensing component. The system control component 110 can be communicatively connected with data repositories, including a patient data repository 118 and a system data repository 120.

The software or instructions executed by the system control component can control the system 100 functions, verify the safety mechanisms, and the service and calibration functions. The control system component 110 can be in communication with a machine-readable medium which can be static memory on which is stored one or more sets of instructions (e.g., software) embodying any one or more of the methodologies or functions described herein, including those methods illustrated herein. The instructions may also reside, completely or at least partially, within the system data repository, static memory, or within the processor, or a combination thereof, during execution thereof by the system 100. The system data repository and patient data repository and the processor also may constitute machine-readable media.

The patient data repository 118 and the system data repository 120 can be a solid-state drive, hard drive or other memory device. The patient data repository 118 can store patient-related data and treatment parameters, such as patient records, treatment session details, and disease documentation and photos. The system data repository 120 stores all system-related data and parameters, such as the system log, x-ray calibration data, and system diagnostics results. The patient data repository 118 and the system data repository 120 can be discrete devices or physically combined. One or more partitions can be used if the repositories 118 and 120 are combined, such as a single repository. Both data repositories will be mirrored and backed up to a secured and encrypted HIPAA-compliant cloud storage medium.

One example of a robotic IORT system 200 is shown in FIG. 2. The system 200 can include a base unit 201 with various components mounted thereon or connected therewith. These components can include a robotic arm 202, a radiotherapy treatment device 216, a saline reservoir 212, a saline control element 214, and a system control component 210. The base unit can also include an optical imaging component 232, an ultrasound component 234, and a data storage device 236 for storing patient and/or system data. The base unit 201 is advantageously a compact unit such as one with a 30"×30" footprint and can be mounted on casters 211 for ease of maneuverability. The base unit 201 can include a power lead for optionally providing power to all of the components housed in or connected to the base unit 201. In this regard, the base unit 201 can contain one or more computers 217 for controlling the system 200 and/or analyzing and processing data obtained from the system 200 components. A monitor 218 can also mounted to the base unit 201 for a user interface. Likewise, a terminal or an input device such as a keyboard or mouse, can be included.

A mount 203 is provided on the base unit 201 for mounting the robotic arm 202. The robotic arm 202 can include a treatment head 224 which can include removable or movable applicators for applying IORT. The robotic arm 202 is articulated with appropriate robotic joints or articulation members 204 under the control of the system control component 210. Although not shown in FIG. 2, additional articulations can also be provided at different points of robotic arm 202 to increase a number of degrees of freedom 225 of placing, orienting and moving treatment head 224. Moreover, the number of articulation points illustrated in FIG. 2 is solely for ease of illustration. The present disclosure contemplates that the any number of articulation points between mount 203 and treatment head 224 can be provided so as to provide any number of degrees of freedom in robotic arm 202 as may be required for dynamically positioning and orienting the treatment head with respect to the patient to compensate for patient body movement. A saline conduit 222 can facilitate communication of saline from the reservoir 212 and saline control component 214 to the treatment head 224. Similarly, power and/or control signals can be communicated from the radiotherapy treatment device 216 to the treatment head 224 to control and facilitate operation of the X-ray tube (not shown in FIG. 2).

The patient motion sensing and tracking described herein is advantageously implemented through the integration of physical sensing means, optical sensing means or both. The X-ray treatment head 224 can be directly mounted on or attached to the robotic arm 202. Consequently, the patient tissue movement exerted on the treatment head can be sensed through direct miniscule physical pressure that is transmitted from the treatment head to the robotic arm. These forces can be defined by associated force vectors aligned with orthogonal x, y and z coordinate axes. The force sensing can be facilitated by physical sensors 242, 244, 246, 248 located in any of several positions throughout the robotic arm. For example, in some scenarios, the physical sensors can be comprise torque sensors associated with each of a plurality of robot arm joints 204. The physical sensors can be a combination of one or more various types, such as piezo-electric, gyroscopic, solid state, and other mechanisms and materials.

To facilitate tracking of patient motion, one or more fiducial markers 226 can be optionally be placed on portions of a patient's body. In some scenarios, the fiducial markers can comprise an optical type of fiducial markers that facilitate optical tracking of position associated with the fiducial marker. The motion of the fiducial markers can be monitored by sensors 228. The sensors 228 may be disposed on a portion of the robotic arm 202 or on a sensor supporting structure 230 which provides good visibility of the patient upon whom IORT is to be performed. The sensors 228 can comprise any type of sensor suitable for monitoring patient motion. For example, in the case where the fiducial markers are of an optical type, LIDAR methods can be used to precisely detect the location of each fiducial marker. Of course, embodiments are not limited in this regard and any other suitable type fiducial marker and associated sensing system can be used. The sensor outputs are monitored by the system control component 210 and processed by one or more motion analyzing software components (tracking system software).

The tracking system software will be periodically provided with updated data from the physical sensor information received from physical sensors 242, 244, 246, 248. Concurrently, the tracking system software is also advantageously provided with fiducial marker position information generated from one or more sensor(s) 228. The tracking system software will use the received information to generate an immediate correcting x, y, z coordinate update command for the robotic arm which reflects the subtle movement of the patient tissue. The robotic arm, subsequently, shall move to the new synchronized x, y, z coordinate/location to correspond with the patient's tissue motion. This motion correction mechanism will advantageously run in a perpetual cyclical loop to constantly sense and follow the patient tissue motion generated by respiratory or other bodily functions.

Based on such analysis, the system control component 210 controls the robotic arm 202 to ensure that the treatment head 224 is moving in precise synchronization with the patient movement. For example, the treatment head can rise and fall with the respiratory action of the patient.

The treatment head 224 is shown in greater detail in FIG. 3. The treatment head can comprise an elongated tubular member 304 formed of a rigid material. The tubular member 304 is secured to an end of the robot arm by means of a base 302 comprising suitable mounting means. A balloon 306 is secured to a treatment end of the tubular member 304 by means of a collar 305 or other suitable attachment mechanism so that the balloon encloses an X-ray tube 314. Power to the X-ray tube is provided by leads 316 which pass through a sealing member 322. Ports 312*a*, 312*b* respectively facilitate attachment of fluid conduits 310*a*, 310*b*. The fluid conduit 310*a* allows a flow of liquid (e.g., saline) to the internal space 326 defined within the balloon. The fluid conduit 310*b* allows a flow of liquid (e.g., saline from the internal space 326. In an example scenario, electrical connections for operation of the X-ray tube can be provided on an end of the robotic arm adjacent to where the base 302 is attached. The leads 316 can be connected to the electrical connections on the robot arm to provide electrical power to the X-ray tube 314. Likewise, saline fluid ports (not shown) can be provided on the robotic arm. The conduits 310*a*, 310*b* can be connected to the fluid ports disposed on the robotic arm to communicate saline fluid to and from the internal space 326 of the balloon. The sealing member 322 prevents saline fluid communicated to the balloon from escaping a distal chamber 324 which may be in fluid communication with the interior space 326 of the balloon 306.

An imaging head 320 can be included on the tubular member to provide for remote operation or for documentation of treatment. A separate imaging head 330 can be disposed inside the balloon 306. Alternatively, or in addition thereto, a fiber optic member 318 can be provided within the interior of the tubular member 304. The fiber optic can extend to the internal space 326 to provide a visual image of the X-ray source during IORT setup and operations. Imaging heads 320, 330 can include components needed for supporting an imaging modality. For example, referring back to FIG. 1, a first imaging head 320 can be provided that includes image capture device 122. The second imaging head 330 can include ultrasound transducer 106. However, the present disclosure also contemplates combined functionality. That is, a single imaging head 320, 330 can incorporate ultrasound transducer 106 and image capture device 122.

In some scenarios it can be advantageous to include one or more patient motion sensors 328 disposed on the treatment head to monitor movement of a patient during IORT operations. However, the one or more sensors 328 are not required to be present on treatment head and can instead be disposed on the robotic arm or other structure to facilitate motion monitoring.

Figure 4:
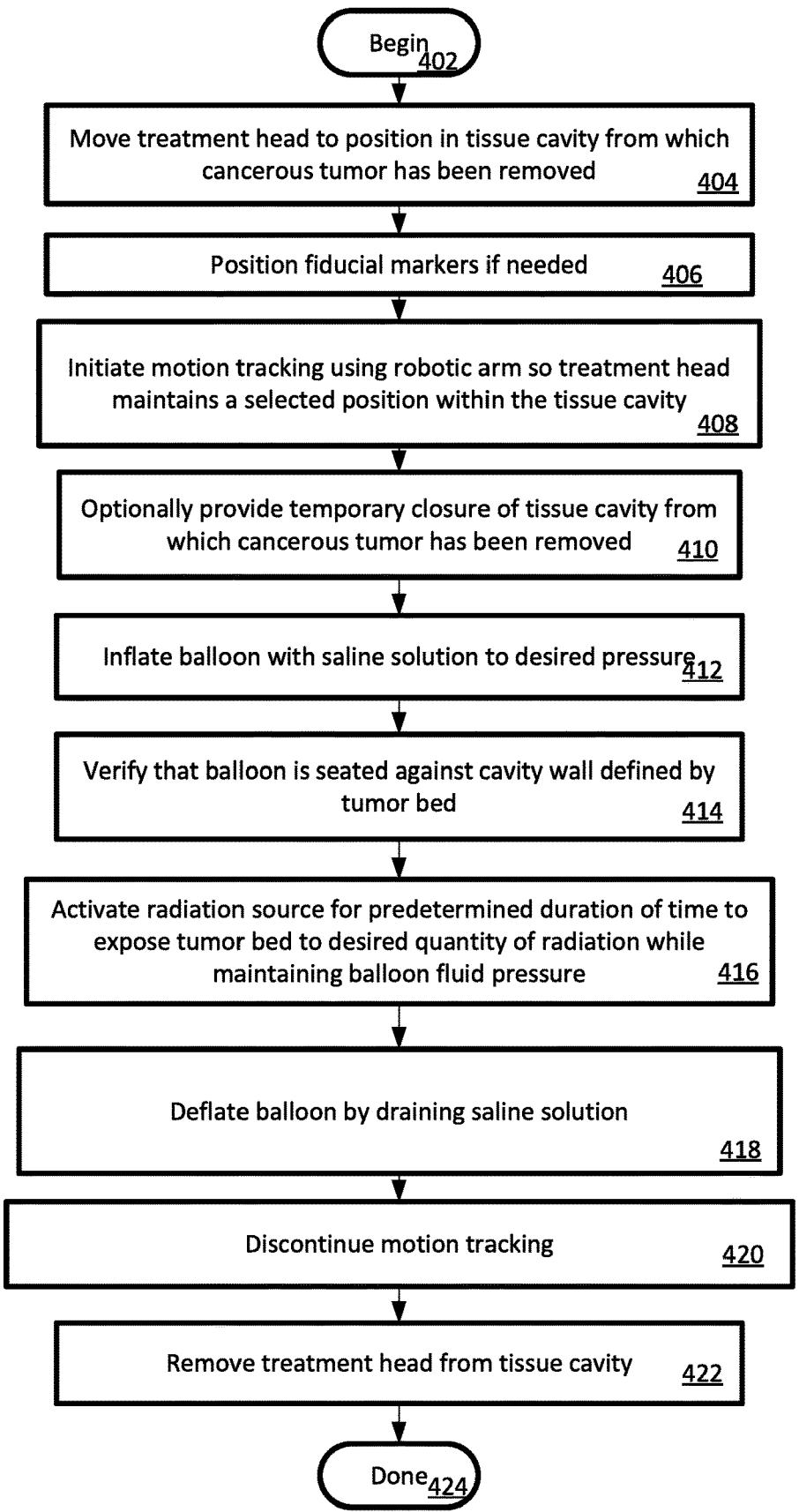
FIG. 4 is a drawing that is useful for understanding a process for robotic IORT.

Referring now to the flowchart of FIG. 4 an exemplary process for robotic IORT is described. The process begins at 402 and continues to 404 when a treatment specialist moves the treatment head so that it is positioned within a tissue cavity from which a cancerous tissue has been removed. The process then continues to step 406 where one or more fiducial markers are optionally positioned on the body of the patient. The use of fiducial markers is optional but can sometimes be helpful to facilitate motion tracking, depending on the type of sensing. At 408 the motion tracking function of the robotic arm can be initiated so the treatment head maintains a selected position within the tissue cavity. At 410, the surgeon can provide a temporary closure of the tissue cavity for purposes of facilitating robotic IORT. After the temporary closure, the IORT treatment balloon is inflated at 412 to a predetermined pressure using the saline solution. At this point, the surgeon can use one or more visualization tools to verify 414 that the walls of the balloon are uniform seated against the cavity wall defined by the tumor bed.

Once satisfied that the balloon is properly inflated and that the radiation source is in a satisfactory position, the radiation source can be activated at 416 for a predetermined period of time. Upon completion of the radiation treatment, the balloon is deflated at 418. Motion tracking can be discontinued at 420 after which the treatment head is removed from the tissue cavity at 422. The process can then ends at 424 or other treatments can be performed.

Figure 5:
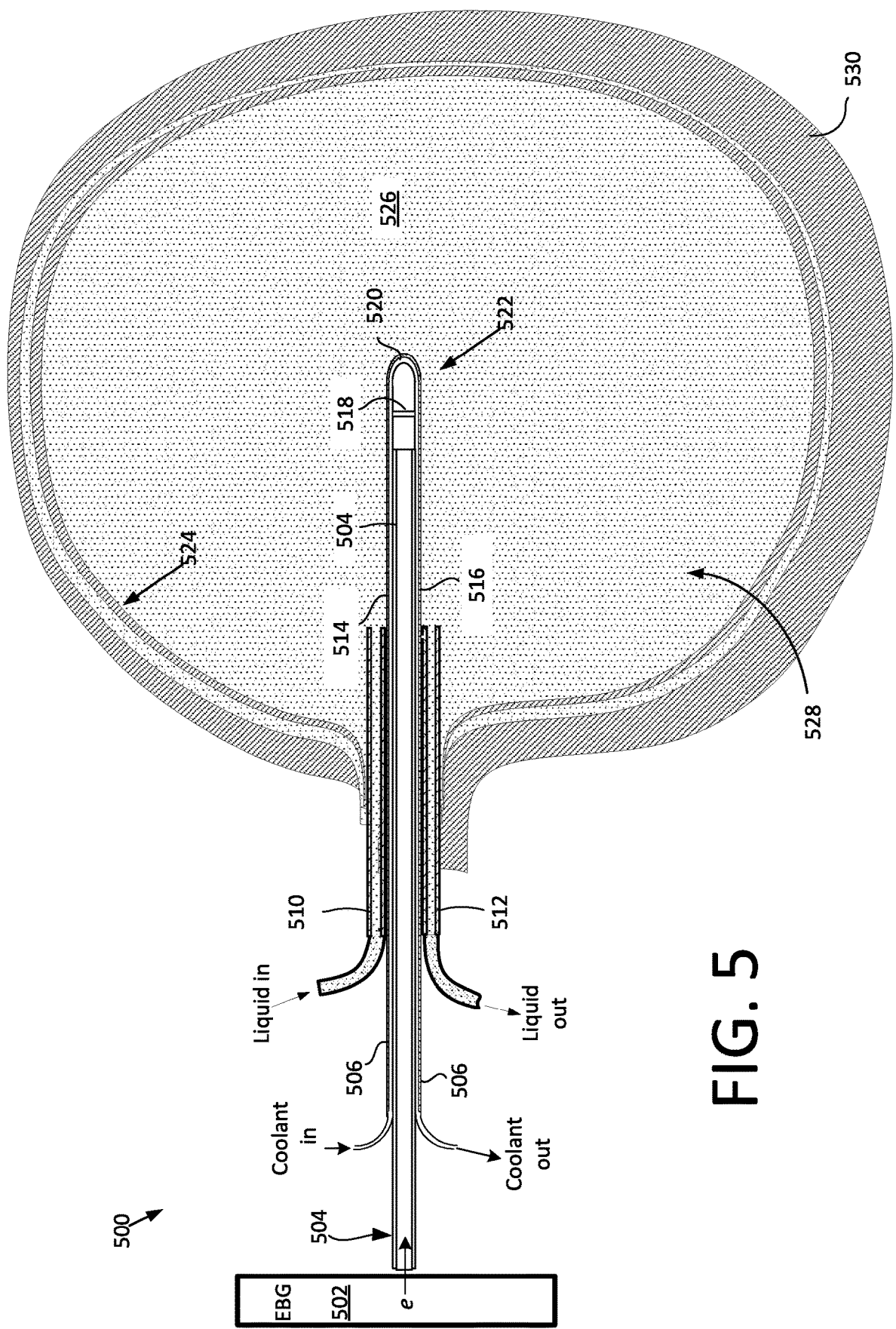
FIG. 5 is a drawing that is useful for understanding an alternative implementation of a treatment head which can be used for robotic IORT using a robotic arm.

Turning now to FIG. 5 there is shown an alternative type of IORT X-ray source 500 which can be used with the robotic IORT system described herein. Briefly, the system comprises an electron beam gun (EBG) 502 and a drift tube 504 which is supported on an end of the robotic arm 202 distal from the base. An IORT X-ray treatment head 522 resides at an end of the drift tube, distal from the EBG. The drift tube 504 is comprised of a conductive material such as stainless steel. Alternatively, the drift tube can be comprised of a ceramic material such as alumina or aluminum nitride with a conductive inner lining. The hollow inner portion of the drift tube is maintained at a vacuum pressure (e.g. a suitable vacuum pressure for purposes of embodiments described herein can be in the range below about 10-5 torr or particularly between about 10-9 torr to 10-7 torr).

Electrons e comprising an electron beam are accelerated by the EBG toward an X-ray target 518. These electrons will have significant momentum when they arrive at the entry aperture of the drift tube. The hollow interior of the drift tube is maintained at a vacuum pressure and at least the inner lining of the tube is maintained at ground potential. Accordingly, the momentum imparted to the electrons by EBG 502 will continue to ballistically carry the electrons down the length of the drift tube at very high velocity (e.g. a velocity approaching the speed of light) toward the X-ray target 518.

It will be appreciated that as the electrons are traveling along the length of the drift tube 504, they are no longer electrostatically accelerated.

The X-ray target 518 is comprised of a disk-shaped element which is disposed transverse to the direction of electron beam travel. For example, the disk-shaped element can be disposed in a plane which is approximately orthogonal to the direction of electron beam travel. In some embodiments, the X-ray target can enclose an end portion of the drift tube distal from the electron gun to facilitate maintenance of the vacuum pressure within the drift tube. The X-ray target 518 can be almost any material, however it is advantageously comprised of a material such as molybdenum, gold, or tungsten which has a high atomic number so as to facilitate the production of X-rays at relatively high efficiency when bombarded with electrons.

In other respects the arrangement shown in FIG. 5 is similar to that described herein with respect to FIG. 3. An interstitial space between the X-ray source (i.e., treatment head 522) and a wound cavity can be filled with saline fluid 526 disposed within a fluid bladder 524. The fluid bladder can be an elastic balloon-like member which is inflated with a fluid 526, such as saline, so as to fill an interstitial space 528 between the X-ray source and a tissue wall 530 (e.g. a tissue wall comprising a tumor bed). Fluid conduits 510, 512 disposed in or on the robotic arm 202 can facilitate a flow of fluid to and from the interior of the fluid bladder. Such an arrangement can help enhance the uniformity of irradiation of the tumor bed by positioning the entire tissue wall a uniform distance away from the X-ray source to facilitate a more consistent radiation exposure. The generation of X-rays at X-ray target 518 can generate substantial amounts of heat. So in addition to the fluid 526 which fills the interstitial space, a separate flow of coolant can be provided to the treatment head through coolant conduits 506.

The various components comprising the X-ray source 500 (e.g., EBG 502, the drift tube 504, and treatment head 522) can be mounted on the robotic arm. The position of the X-ray source can be controlled as described with respect to FIGS. 1-4 so that movement of the X-ray source is coordinated with natural body motion of the patient undergoing treatment. Of course, the methods for robotic IORT are not limited to the particular IORT X-ray radiation sources described above. Instead, any suitable X-ray source now known or known in the future can be used to facilitate the robotic IORT methods and systems described herein.

Figure 6:
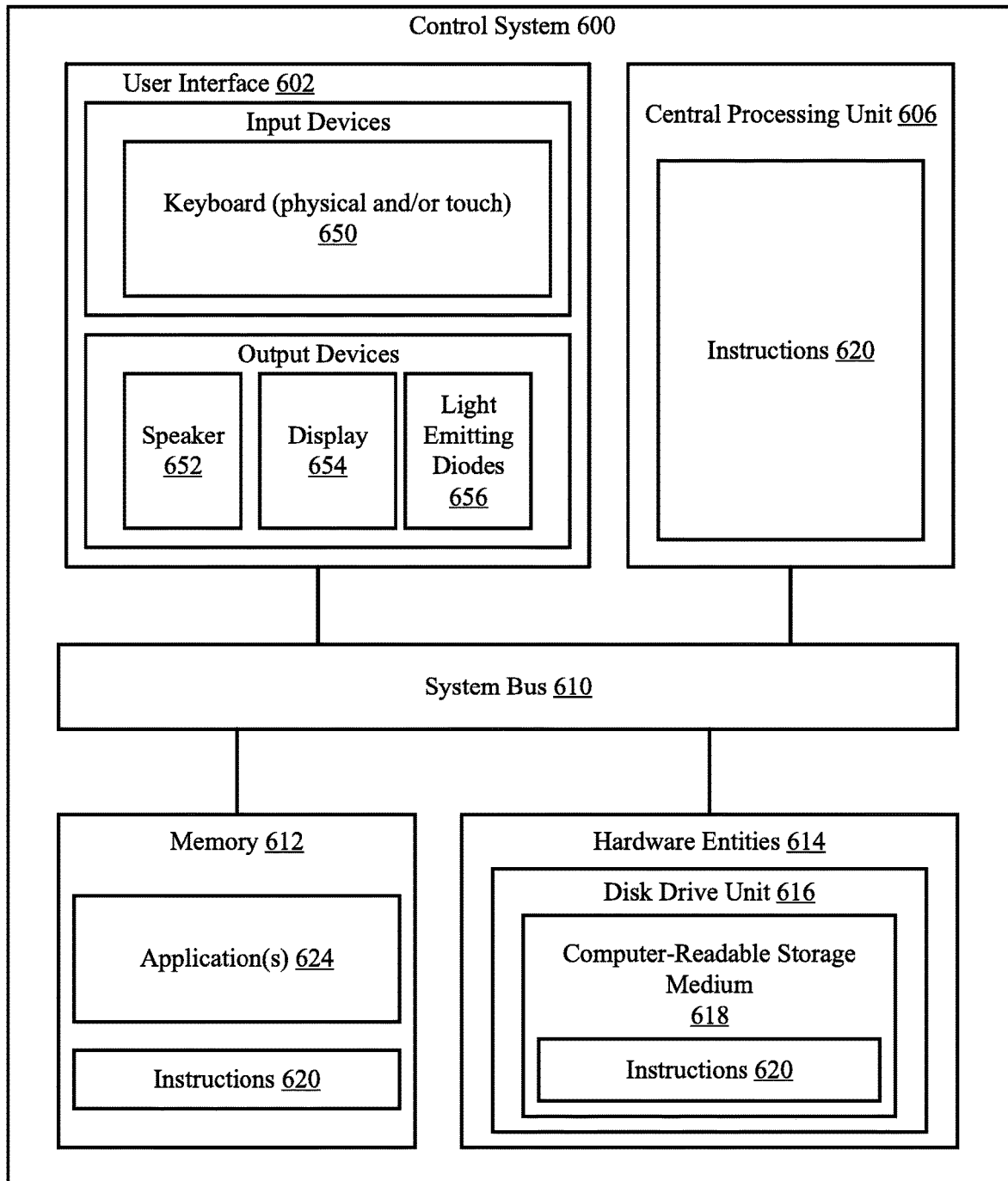
FIG. 6 is a block diagram that is useful for understanding a control system which can be used for facilitating robotic IORT as described herein.

Referring now to FIG. 6, there is provided an illustration of an exemplary control system 600 which can be used for controlling a robotic IORT system as described herein. The control system can include, but is not limited to, machines (or computing devices) running a Windows OS (e.g., a personal computer or server). Such machines (or computing devices) are well known in the art, and will not be described in detail herein. Still, it should be understood that such machines are modified to implement all or a portion of the methods described herein. Such modifications can include software modifications, hardware modification or a combination of both.

Control system 600 may include more or less components than those shown in FIG. 6. However, the components shown are sufficient to disclose an illustrative embodiment implementing the present solution. The hardware architecture of FIG. 6 represents one embodiment of a representative control system or computing device configured to facilitate the IORT tracking control operations described herein.

Some or all the components of the control system 600 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 6, the control system 600 comprises a user interface 602, a Central Processing Unit ("CPU") 606, a system bus 610, a memory 612 connected to and accessible by other portions of computing device 600 through system bus 610, and hardware entities 614 connected to system bus 610. The user interface can include input devices and output devices, which facilitate user-software interactions for controlling operations of the computing device 600. The input devices include, but are not limited, a physical and/or touch keyboard 650. The input devices can be connected to the computing device 600 via a wired or wireless connection (e.g., a Bluetooth® connection). The output devices include, but are not limited to, a speaker 652, a display 654, and/or light emitting diodes 656.

At least some of the hardware entities 614 perform actions involving access to and use of memory 612, which can be a Radom Access Memory ("RAM"), a disk drive and/or a Compact Disc Read Only Memory ("CD-ROM"). Hardware entities 614 can include a disk drive unit 616 comprising a computer-readable storage medium 618 on which is stored one or more sets of instructions 620 (e.g., software code) configured to implement one or more of the methodologies, procedures, or functions described herein. The instructions 620 can also reside, completely or at least partially, within the memory 612 and/or within the CPU 606 during execution thereof by the computing device 600. The memory 612 and the CPU 606 also can constitute machine-readable media. The term "machine-readable media", as used here, refers to a single medium or multiple media (e.g., a centralized or distributed database, and/or associated caches and servers) that store the one or more sets of instructions 620. The term "machine-readable media", as used here, also refers to any medium that is capable of storing, encoding or carrying a set of instructions 620 for execution by the control system 600 and that cause the control system 600 to perform any one or more of the methodologies of the present disclosure.

In some scenarios, the hardware entities 614 include an electronic circuit (e.g., a processor) programmed for facilitating control over the robotic arm. In this regard, it should be understood that the electronic circuit can access and run application(s) 624 installed on the computing device 600.

Figure 7:
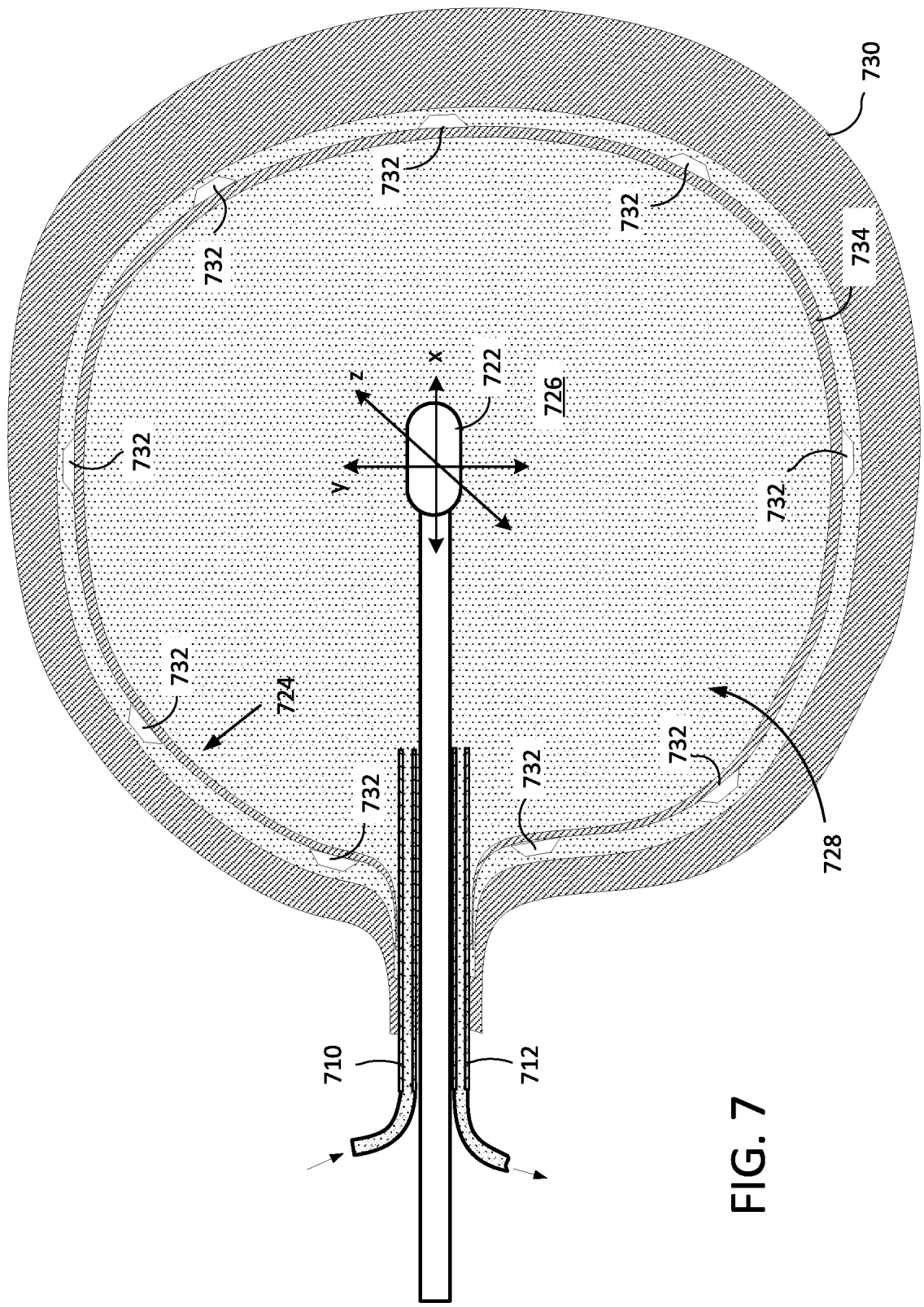
FIG. 7 is a drawing that is useful for understanding an X-ray dosimetry sensing system and method.
Figure 8:
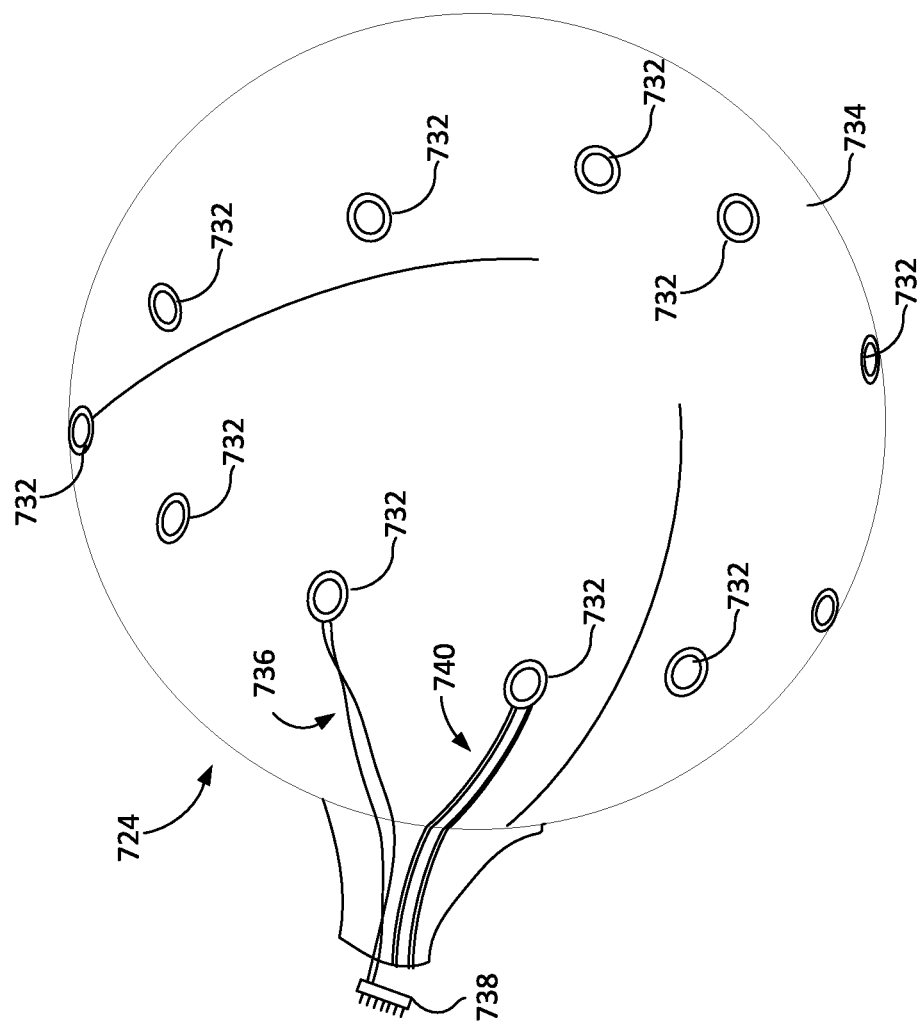
FIG. 8 is a drawing that is useful for understanding an arrangement of X-ray dosimetry sensors.

Referring now to FIGS. 7 and 8, there is shown a balloon 724 which can be used for IORT with any of the X-ray sources described herein. The balloon 724 can be formed of a material such as Nylon, Pebax, PET, or polyurethane. Further the balloon material can be comprised of a blends and/or compositions of such materials. For example, a single layer, dual layer or multiple layers of such materials are possible. The balloon material(s) is advantageously selected so that it is radiolucent with respect to the range of X-ray radiation to be applied.

The arrangement shown in FIGS. 7 and 8 is similar to that described herein with respect to FIGS. 3 and 5. An interstitial space between the X-ray source (i.e., treatment head 722) and a wound cavity can be filled with fluid 726 (e.g., saline fluid) disposed within the bladder or balloon 724. The balloon or fluid bladder can be an elastic balloon-like member which is inflated with a fluid, such as saline, so as to fill an interstitial space 728 between the X-ray source and a tissue wall 730 (e.g. a tissue wall comprising a tumor bed). Fluid conduits 710, 712 disposed can facilitate a flow of fluid to and from the interior of the balloon.

A plurality of X-ray radiation sensor elements (XRSE) 732 are disposed on the exterior surface 734 of the balloon 724. In an alternative embodiment shown in FIG. 9, the XRSE 723 can be integrated within or disposed between one or more layers comprising the balloon. The XRSE 732 are disposed at a plurality of predetermined locations. In some scenarios, these locations can be aligned with each of a plurality of orthogonal axis which define an x, y and z coordinate system. In such a scenario, the X-ray radiation source associated with the treatment head can be generally aligned at the origin where the orthogonal axis intersect. In other scenarios, the plurality of XRSE can be aligned with a plurality of points which define an ovoid or roughly spherical grid. The term ovoid or spherical grid as used herein can be a set of points which are uniformly (or semi-uniformly) disposed over the surface of an ovoid or approximately spherical shape as defined by the balloon.

A device comprising any suitable type of X-ray sensing technology can employed for implementing the XRSE disclosed herein. For example, these detectors can be comprised of solid state semiconductor materials (usually based around silicon or germanium chips), silicon drift detectors (SDD), or PIN diode detectors. PIN diode detectors have the advantage of utilizing a much smaller detector element as compared to other types of X-ray detection devices.

Solid state X-ray detectors are well-known in the art and will not be described here in detail. However, it should be noted that there are various types of semiconductor materials which can be used for implementing solid state X-ray detectors, including without limitation silicon (Si), germanium (Ge), and cadmium telluride (CdTe). X-ray photons which are incident on the semiconductor will interact with the material to produce electron-hole pairs. The electron-hole pairs which are produced will increase proportionally with radiation intensity. Accordingly, the electron hole pairs can generate an electric signal to indicate the intensity of the X-ray radiation.

Figure 9:
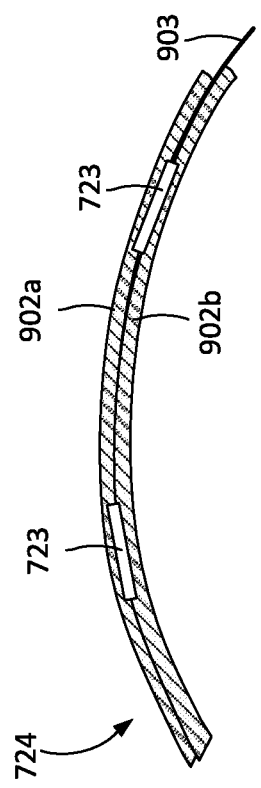
FIG. 9 is a drawing that is useful for understanding an X-ray sensor which is integrated within the material or material layers comprising a balloon.

Power and/or signal communications between the plurality of XRSE and the control system can be facilitated by various means. In some scenarios, conductive wire leads or optical fiber can be used to facilitate such functions. These communication/power leads 736 can extend from each XRSE 732 to a suitable connector 738 through which the signals from each XRSE can be received by the control system. In some scenarios, the signal communication/power leads can be separate from the balloon. However, in other scenarios, the communications/power leads 740 can be integrated in or disposed directly on the surface of the balloon using printed circuit methods. In such scenarios, the leads can be fixed to the outer surface of the balloon as shown in FIG. 8. Alternatively, leads (e.g., power/communication leads 903) can be integrated with or disposed within material layers (e.g. between material layers 902a, 902b) forming the balloon as shown in FIG. 9. In some cases, the power/communication leads can be formed of a material which flexes or stretches with the surface of the balloon so that the communication/power leads remain intact as the balloon expands and contracts.

Wireless communications between the XRSE and the control system are also anticipated with the current solution. In such scenarios, each XRSE can have a specific logical address for data communications to and/or from the control system. One or more of the XRSE can be connected to a wireless communication circuit for transmitting measured X-ray intensity data to the control system. In some scenarios, the wireless communication circuit can be integrated with the balloon. The one or more wireless communications circuits described herein can be implemented using any suitable method, including but not limited to well-known schemes such as Bluetooth® or Near Field Communication methods. In some scenarios, the XRSE could utilize energy harvesting technology to derive power from the X-ray energy emanating from the X-ray source.

When certain materials are exposed to X-rays ionization will occur which involves the ejection of one or more electrons from the atom. The removal of an electron results instability of the electronic structure, thereby causing electrons in higher orbitals to "fall" into lower orbits. This activity releases energy in the form of a photon. Thus, radiation is emitted which has specific characteristic energy determined by the material. This activity is commonly referred to as fluorescence.

Figure 10:
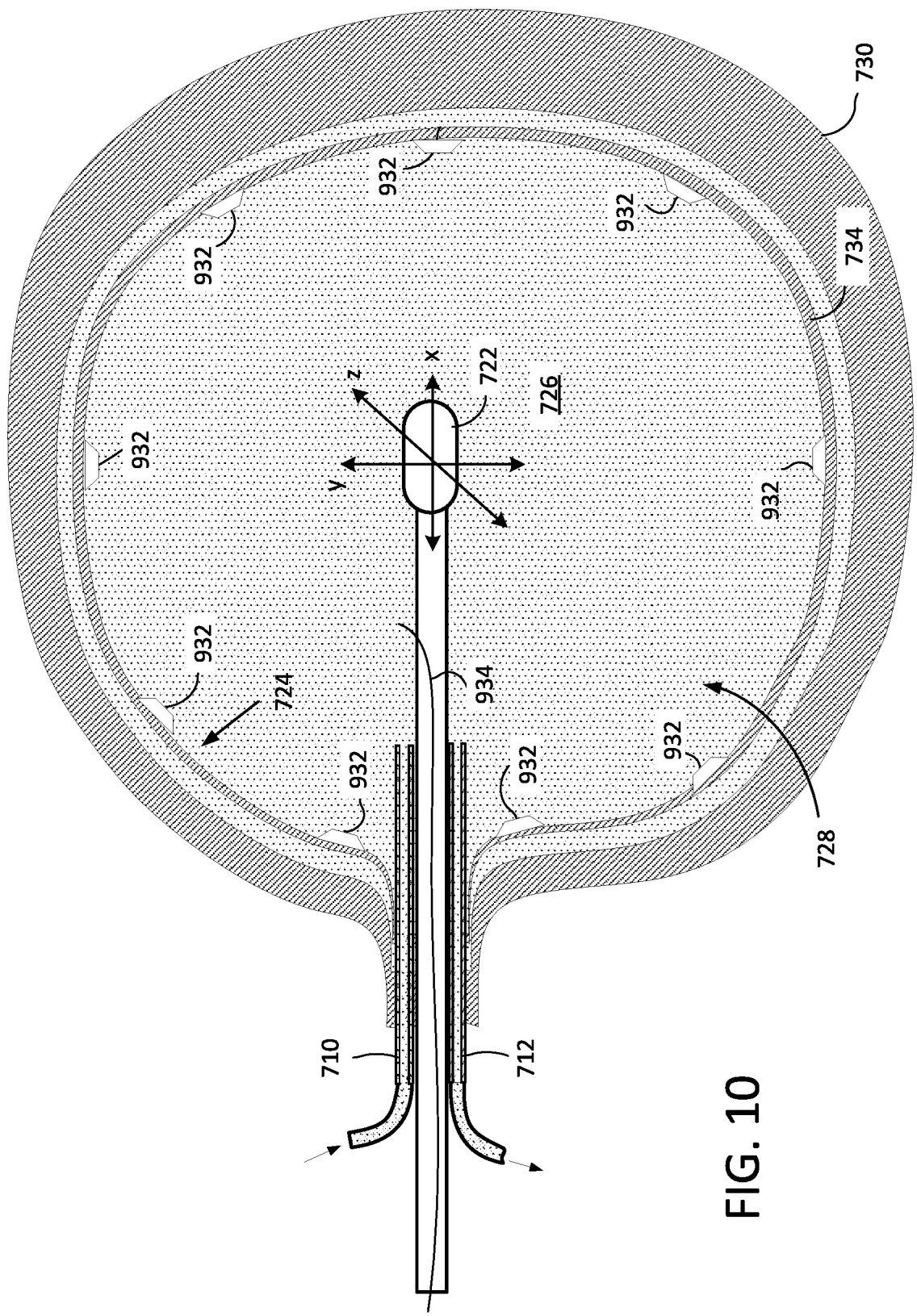
FIG. 10 is a drawing that is useful for understanding an alternative embodiment X-ray sensing element.

Referring now to FIG. 10, there is illustrated an alternative embodiment in which the XRSE 932 are responsive to X-ray energy such that each XRSE 932 will fluoresce or radiate electromagnetic energy. In some scenarios, the intensity of the fluorescence will correspond to a level of received X-ray energy. As the X-ray energy increases, the XRSE will fluoresce more intensely. Conversely, as the X-ray energy decreases, the XRSE will fluoresce less intensively. Alternatively, the XRSE can be configured to undergo a color change in response to exposure to X-ray energy. One or more image capture devices can utilize optical fiber(s) 934 or other imaging element to capture images showing the interior surface of the balloon. Consequently, a treatment practitioner can receive a visual indication of X-ray dose applied to all surfaces of the balloon interior. The treatment dose can be evaluated visually based on sensor color change, or based on a duration of time that fluorescence has occurred while observing the X-ray application. In some scenarios, the color change and/or intensity of fluorescence can be monitored and/or recorded by the control system. Using image processing techniques, each XRSE can be marked by the control system and assigned a unique index number or address and can thereafter be monitored by the control system. An advantage of this approach is that it greatly simplifies the XRSE, and the necessary couplings for power and data communications. However, additional image processing is necessary to capture and evaluate the X-ray energy received by each of the XRSE 932.

In some scenarios, the XRSE 932 described herein can operate in a manner that is similar to the operation of X-ray dosimeter badges used by persons who work with X-ray equipment. As is known, the material (aluminum oxide) used with some such X-ray dosimeter badges will give off visible light when exposed to X-ray radiation and then irradiated with a specific wavelength of laser light. The released energy of excitation can be measure to determine radiation dose. Accordingly, it is anticipated that in some scenarios, a laser exciter source can be provided within the balloon to facilitate the X-ray dosimetry measurements described herein.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

I claim:

1. A method for real-time X-ray dosimetry, comprising
disposing an X-ray treatment head within an inflatable balloon;
inflating the balloon;
using the X-ray treatment head to apply X-ray energy to a treatment surface external of the balloon;
detecting an X-ray dose delivered by the X-ray treatment head a plurality of sensing elements which are attached at a plurality of different locations on an inner surface of a peripheral wall of the balloon;
using an image capture device disposed within the balloon to capture an image of the inner surface and the plurality of sensing elements disposed on the inner surface;
using an electronic control system to assign a unique index value to each of the plurality of sensing elements contained in the image;
monitoring with the electronic control system each of the plurality of sensing elements with an assigned index value to obtain a visual indication associated with each of the plurality of sensing elements contained in the image; and
using the visual indication of each of the plurality of sensing elements to determine the X-ray dose delivered at the plurality of different locations.

2. The method according to claim 1, wherein the plurality of different locations are respectively aligned with a plurality of points defined on the peripheral wall of the balloon where a plurality of orthogonal axes, centered on the X-ray treatment head, intersect the inner surface of the balloon, when the balloon is inflated.

3. The method according to claim 1, wherein the plurality of different locations define an ovoid or spherical grid pattern on the inner surface of the balloon, when the balloon is inflated.

4. The method according to claim 1, further comprising communicating image data from the image capture device to the electronic control system.

5. The method according to claim 4 wherein the image data is communicated from the image capture device to the electronic control system using at least one component selected from the group consisting of a conductive wire lead, an optical fiber, and a wireless data transceiver.

6. The method according to claim 1, wherein the visual indication associated with each of the plurality of sensing elements is a fluorescence of the plurality of sensing elements when exposed to the X-ray energy.

7. The method according to claim 6, wherein determining the X-ray dose delivered at the plurality of different locations is based on an intensity of fluorescence exhibited by each of the plurality of sensing elements.

8. The method according to claim 1, wherein the visual indication associated with each of the plurality of sensing elements is a color change of the plurality of sensing elements, and wherein determining the X-ray dose delivered at the plurality of different locations is based on the color change exhibited by each of the plurality of sensing elements.

9. A system for real-time X-ray dosimetry, comprising
an inflatable balloon configured to receive within an interior thereof an X-ray treatment head from which X-rays are configured to be emitted;

a plurality of sensing elements attached to a peripheral wall which forms an inner surface of the balloon, the plurality of sensing elements responsive to X-ray energy;

an image capture device disposed within the balloon and configured to capture an image of the inner surface and the plurality of sensing elements disposed on the inner surface; and an electronic control system configured to
assign each of the plurality of sensing elements contained in the image with a unique index value,
monitor each of the plurality of sensing elements having an assigned index value to obtain at least one visual indication associated with each of the plurality of sensing elements contained in the image, and
based on the at least one visual indication, determine an X-ray dose delivered at a plurality of different sensing locations respectively associated with the plurality of sensing elements.

10. The system according to claim 9, wherein the plurality of different sensing locations are aligned with locations where a plurality of orthogonal axes having an origin at an approximate center of the balloon when inflated, intersect the inner surface of the balloon.

11. The system according to claim 9, wherein the plurality of different sensing locations define an ovoid or spherical grid pattern on the inner surface of the balloon, when the balloon is inflated.

12. The system according to claim 9, wherein the image capture device is configured to facilitate communication of image data from the image capture device to the electronic control system.

13. The system according to claim 12, wherein the image data is communicated from the image capture device to the electronic control system using an information communication component selected from the group consisting of a conductive wire lead, an optical fiber, and a wireless data transceiver.

14. The system according to claim 9, wherein the at least one visual indication associated with each of the plurality of sensing elements is a fluorescence or change color of the plurality of sensing elements when exposed to the X-ray energy.

15. The system according to claim 14, wherein the electronic control system is configured to evaluate the fluorescence or color change as the basis for determining the X-ray dose delivered at each of the plurality of sensing elements.

* * * * *